US008535922B2

(12) United States Patent
Nishimoto et al.

(10) Patent No.: US 8,535,922 B2
(45) Date of Patent: Sep. 17, 2013

(54) METHOD FOR PRODUCING ETHANOL

(75) Inventors: Tetsuro Nishimoto, Hiroshima (JP);
Kiyohiro Nishimoto, Hiroshima (JP);
Tsutomu Morinaga, Hiroshima (JP)

(73) Assignee: Hokto Corporation, Nagano (JP)

( * ) Notice: Subject to any disclaimer, the term of this patent is extended or adjusted under 35 U.S.C. 154(b) by 364 days.

(21) Appl. No.: 12/735,596

(22) PCT Filed: Jan. 13, 2009

(86) PCT No.: PCT/JP2009/050267
§ 371 (c)(1),
(2), (4) Date: Sep. 7, 2010

(87) PCT Pub. No.: WO2009/096215
PCT Pub. Date: Aug. 6, 2009

(65) Prior Publication Data
US 2010/0330641 A1    Dec. 30, 2010

(30) Foreign Application Priority Data
Feb. 1, 2008    (JP) .................. 2008-022982

(51) Int. Cl.
*C12P 7/10*    (2006.01)
*C12N 9/00*    (2006.01)
*C12N 9/42*    (2006.01)
*C12N 1/20*    (2006.01)
*C12N 15/00*    (2006.01)
*C07H 21/04*    (2006.01)

(52) U.S. Cl.
USPC ........ 435/165; 435/183; 435/209; 435/252.3; 435/320.1; 536/23.2

(58) Field of Classification Search
None
See application file for complete search history.

(56) References Cited

FOREIGN PATENT DOCUMENTS
JP    2000-246225 A    9/2000
JP    2004-215648 A    8/2004
JP    2006-111593 A    4/2006

OTHER PUBLICATIONS

Karimi et al. Biotechnol Lett. Sep. 2005;27(18):1395-400.*
Garzlllo et al. Applied Microbiology and Biotechnology, vol. 42, Issue 2-3, pp. 476-481.*
Mohammed J. Taherzadeh et al., "Ethanol from Lignocellulosic materials: pretreatment, acid and enzymatic hydrolyses, and fermentation", ACS symposium series, 2004, pp. 49-68.
Ryosuke Nakajima et al., "Enzymic Saccharification of Waste Substrate including Unused Tree Species (*Alnus japonica, Zelkova serrata*) for Edible Mushroom Cultivation and Alchohol Fermentation Thereof", Abstracts of Annual Meeting of the Japan Wood Research Society (CD-ROM), 2006, vol. 57, pp. 0009.
Tsutomu Morinaga, "Dioxin Decomposition by waste Substrate of *Hypsizygus marmoreus* (Peck) Bigelow", Mizu, Feb. 1, 2000, vol. 42, No. 3, pp. 16-17.
Shuhei Kaneko et al., "Shinrin Ecosystem ni Okeru Shinrin Biseibutsu no Kino Kaimei to sono Oyo ni Kansuru Kenkyu", Heisei 11 Nendo Annual Report of Fukuoka Prefecture Forest Research and Extension Canter, Jul. 31, 2000, pp. 104-106.
Inosuke Saeki, Kinoko Rui no Baiyoho, Kabushiki Kaisha Chikyusha, Jul. 1, 1978, revised 3rd edition, pp. 66-67 lines 14-17.

* cited by examiner

*Primary Examiner* — Christian Fronda
(74) *Attorney, Agent, or Firm* — Rabin & Berdo, P.C.

(57) ABSTRACT

The present invention provides a method for producing an ethanol from a lignocellulose resource efficiently. According to the method for producing the ethanol of the present invention, an enzyme group derived from a mushroom waste substrate has a high activity and can allow cellulose or xylan in the lignocellulose resource to be efficiently converted into glucose or xylose. That is, the lignocellulose resource can be converted into a saccharified solution including the glucose or xylose thereinside. The glucose or xylose in the saccharified solution can be converted into the ethanol by fermentation of yeast or bacterium provided into the saccharified solution. The method for producing the ethanol of the present invention can allow the ethanol to be efficiently produced from the lignocellulose resource.

12 Claims, 1 Drawing Sheet

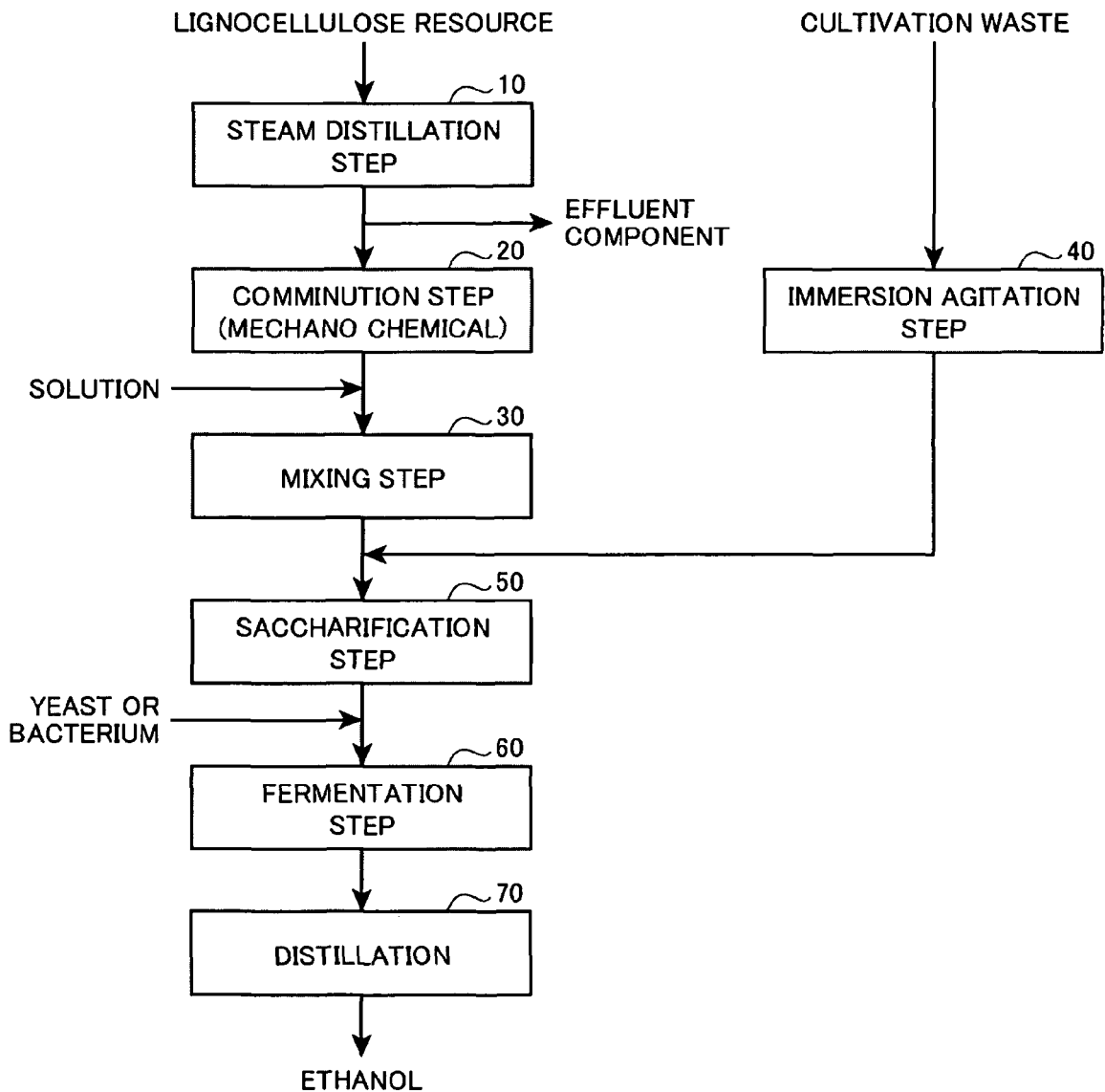

METHOD FOR PRODUCING ETHANOL

FIELD OF THE INVENTION

The present invention relates to a method for producing ethanol from a lignocellulose resource.

DESCRIPTION OF RELATED ART

A lignocellulose resource represents a resource having lignocellulose as a primary component among biologically-derived organic resources except for fossil fuels. For example, Patent Document 1 discloses one of the methods for producing ethanol from the lignocellulose resource by saccharification of cellulose in the lignocellulose resource with an enzyme and fermentation of a saccharified solution obtained by the saccharification.
Patent Document 1: Japanese Unexamined Patent Application Publication No. 2006-111593

SUMMARY OF THE INVENTION

According to Patent Document 1, cellulase is used for saccharification of the cellulose in the lignocellulose resource. However, the cellulase generally available on the market alone or the cellulase coarsely purified has a low activity, causing inefficient saccharification of the cellulose in the lignocellulose resource. In addition, a large amount of the cellulase is needed to process a large amount of the lignocellulose resource, causing cost problems.

The present invention is proposed in consideration of the aforementioned conventional situations and is intended to provide a method for producing ethanol in good yield by efficient saccharification of cellulose or xylan in a lignocellulose resource.

Inventors of the present invention, as a result of dedication to the research, have found that a high cellulase activity and a high xylanase activity are provided in an enzyme group derived from a mushroom waste substrate, and have completed development of the method for producing the ethanol using the enzyme group.

Herein, the mushroom waste substrate represents a substrate used for mushroom cultivation. The mushroom waste substrate is the substrate discarded after cultivation of edible mushrooms such as *Lentinus edodes* (Berk.) Singer, *Flammulina velutipes* (Curt.: Fr.) sing., *Hypsizygus marmoreus* (Peck) Bigelow, *Pholiota nameko* (T. Ito) S. Ito et Imai, *Pleurotus eryngii* (DC.:Fr.) Quel, *Pleurotus ostreatus* (Jacq.: Fr.) Kummer, and western mushrooms. The method for producing the ethanol of the present invention includes: a saccharification step allowing a saccharified solution to be generated from the lignocellulose resource by enzymatic saccharification reaction using an enzyme group derived from the mushroom waste substrate; and a fermentation step allowing the ethanol to be generated by fermentation of the saccharified solution generated by the saccharification step.

According to the method for producing the ethanol of the present invention, the enzyme group derived from the mushroom waste substrate has a high activity and can allow the cellulose or the xylan in the lignocellulose resource to be efficiently converted into glucose or xylose. That is, the lignocellulose resource can be converted into the saccharified solution having the glucose or the xylose thereinside. The glucose or the xylose in the saccharified solution can be converted into the ethanol by fermentation of yeast or bacterium provided into the saccharified solution. The method for producing the ethanol of the present invention can allow the ethanol to be efficiently produced from the lignocellulose resource. Moreover, the waste substrate is residue from mushroom harvest, and the enzyme group such as the cellulase is extracellularly released by hyphae spread in the waste substrate. Accordingly, the usage of such an enzyme group allows a high degradability of the lignocellulose resource compared to the usage of the cellulase available on the market alone, so that the saccharification is efficiently performed. Moreover, the waste substrate is used after the edible mushrooms are harvested, thereby reducing waste of a raw material.

BRIEF DESCRIPTION OF THE DRAWINGS

FIG. 1 is a flowchart illustrating an example procedure for producing ethanol according to the present invention.

DETAILED DESCRIPTION OF PREFERRED EMBODIMENTS

Hereinafter, an embodiment of the present invention will be described in detail. The present invention may, however, be embodied in many different forms and should not be construed as limited to the embodiments set forth herein. The embodiments, therefore, may be modified or varied without departing from the scope of the present invention.

The method for producing the ethanol of the present invention includes seven steps to be conducted with respect to a lignocellulose resource serving as a raw material. The seven steps include: steam distillation step 10; comminution step 20; mixing step 30; immersion agitation step 40; saccharification step 50; fermentation step 60; and distillation step 70.

The lignocellulose resource used for the present invention, for example, includes a wood such as a beech, a eucalyptus, a Douglas pine (or an Oregon pine), a cypress, and a cedar, and a bamboo family such as a bamboo and a bamboo grass. The lignocellulose resource used for the present invention is, however, not limited thereto. For example, the lignocellulose resource includes a material having lignocellulose and a waste substance such as used paper generated from the material having the lignocellulose. Herein, the material having the lignocellulose is, for example, rice straw, wheat straw, a bagasse, and a pulp.

The steam distillation step 10 allows the lignocellulose resource having a prescribed size to be distilled with steam, and allows an essential oil and a hydrophilic component contained in the lignocellulose resource to be flowed out as an effluent component.

The size of the lignocellulose resource used for the steam distillation step 10 can be any size as long as the steam distillation is performed. Moreover, the comminution step 20 can be performed before the steam distillation step 10. Accordingly, the steam distillation can be performed with respect to the lignocellulose resource having a small and uniform size, so that an effluent efficiency of the essential oil and the hydrophilic component can be enhanced.

The lignocellulose resource includes the essential oil having a lipophilic property insoluble in water and the hydrophilic component soluble in water in a cell thereof. The essential oil is a volatile substance, for example, obtained in an oil state or a semi solid state. The hydrophilic component, on the other hand, is a substance such as an organic acid or a saccharide included in the lignocellulose resource.

The steam distillation step 10 allows the essential oil or the hydrophilic component having a low boiling point to be flowed out with the steam, and allows the hydrophilic component having a high boiling point to be flowed out to an outside system with heated steam generated by dissolution of the hydrophilic component in a water-drop in the steam. The heated steam generated by the steam distillation allows the essential oil and the hydrophilic component to be flowed out from the lignocellulose resource. The flow out of the essential oil and the hydrophilic component from the lignocellulose resource can increase an exposed surface area of the cellulose or the xylan, so that the cellulose or the xylan can easily contact the enzyme, thereby accelerating the saccharification of the cellulose or the exylan.

In a case where the lignocellulose resource includes impurities such as soil and dirt, the steam distillation step 10 can allow the impurities to be washed out. Accordingly, a pre-process for removal of the impurities interfering an enzymatic saccharification reaction is not necessary for the saccharification step 50.

The comminution step 20 allows the lignocellulose resource to be mechanically comminuted in such a manner as to be the prescribed size, so that the cellulose or the xlyan in the lignocellulose resource is comminuted or pulverized into fine powder. Accordingly, the comminution step 20 allows the cellulose or the xylan to easily undergo the enzymatic saccharification reaction.

The lignocellulose resource is comminuted to preferably have a size of 2 μm to 100 μm in the comminution step 20. The comminution of the lignocellulose resource in the comminution step 20 can be performed, for example, using a vibrating ball mill, a rotating ball mill, a planetary ball mill, a roll mill, a disk mill, a bead mill, a vane-type high speed rotating mixer, or a homo mixer.

The lignocellulose resource is comminuted until reaching the prescribed size, so that a network structure forming the lignocellulose resource is destroyed in the comminution step 20. Herein, the network structure is formed of the cellulose, a hemicellulose, and lignin. Particularly, the lignin is separated from the cellulose or the xylan, and one portion of microfibril formed by crystallization of the cellulose and the xylan is exposed. Accordingly, the cellulose or the xylan tends to easily contact the enzyme group, and easily undergoes the enzymatic saccharification reaction in the saccharification step 50.

The steam distillation step 10 and the comminution step 20 allow one portion of the microfibril forming the lignocellulose resource to be exposed and allow space among the microfibril to increase, so that the enzyme group becomes easier to contact the cellulose or the xylan. Therefore, the saccharification of the cellulose or the xlyan is accelerated.

The mixing step 30 allows the lignocellulose resource undergone the steam distillation step 10 and the comminution step 20 to be mixed with a solution (also referred to as a liquid medium). Herein, the lignocellulose resource and the solution are mixed to form a mixed solution including pH being adjusted in such manner as to be within an optimum pH range of the enzyme for the enzyme saccharification reaction to be performed in the saccharification step 50.

An amount of the lignocellulose resource to be mixed into the solution in the mixing step 30 is preferably smaller than or equal to forty (40) percent. For example, in a case where the amount of the lignocellulose resource is greater than or equal to fifty (50) percent, the lignocellulose resource in a powder state is simply moisturized and not mixed with the solution to form the mixed solution. Consequently, in a case where the enzyme group is provided in a state that the amount of the lignocellulose resource is greater than or equal to fifty (50) percent, the enzymatic saccharification reaction is not smoothly performed.

The solution to be used in the mixing step 30 can be any solution as long as the enzyme saccharification reaction is not interfered. For example, water or a pH buffer solution can be used as the solution in the mixing step 30. In a case where the pH buffer solution is used as the solution, for example, a pH buffer solution suitable for the optimum pH of the enzyme to be used for the enzymatic saccharification reaction is selected and mixed with the lignocellulose resource. Accordingly, the pH of the mixed solution does not tend to be out of the optimum pH range, and the enzymatic saccharification reaction is smoothly performed in the saccharification step 50.

In a case where the water is used as the solution, for example, the water is mixed with the lignocellulose resource. Subsequently, acid or alkali is provided into the mixed solution, and the pH of the mixed solution is adjusted in such a manner as to be within the optimum pH range of the enzyme.

According to the present invention, the steam distillation step 10 allows the effluent component to be flowed out from the lignocellulose resource, thereby reducing an amount of organic acid and the like causing a change in the pH of the mixed solution by flowing into the system during the enzymatic saccharification reaction. Therefore, the pH of the mixed solution can be adjusted within the optimum pH range with a small amount of the acid or alkali. Moreover, since an amount of the organic acid to be flowed out form the lignocellulose resource is small, the pH of the mixed solution does not tend to be out of the optimum pH range during the enzymatic saccharification reaction. Accordingly, the reaction is smoothly performed.

According to the method for producing the saccharified solution of the present invention, the steam distillation is performed with respect to the lignocellulose resource before the mixing step 30. The steam distillation allows the effluent component such as the essential oil and the hydrophilic component to be flowed out from the lignocellulose resource. The effluent component includes the organic acid and the like included in the lignocellulose resource. For example, in a case where a lignocellulose resource not to be distilled with steam is used to perform an enzymatic saccharification reaction, an organic acid and the like is flowed out in a reacting system, causing an increase in the possibility for pH of a mixed solution to be out of the optimum pH range of the enzyme. Consequently, a large amount of the pH buffer solution or alkali and the like needs to be provided. According to the present invention, on the other hand, the amount of the organic acid and the like is small, so that the pH of the mixed solution is easily adjusted before the enzymatic saccharification reaction and during the enzymatic saccharification reaction.

The immersion agitation step 40 allows the mushroom waste substrate to be dispersed and agitated in a water system solution to extract the enzyme group derived from the mushroom waste substrate. The mushroom waste substrate includes the cellulase group generating glucose by hydrolyzing the cellulose in the lignocellulose resource. The mushroom waste substrate can be used from a time immediately after the mushroom harvest to a time immediately before microbial decomposition by being left. The enzyme group derived from the mushroom waste substrate is obtained by: comminuting the mushroom waste substrate in an appropriate size; dispersing the comminuted mushroom waste substrate in the water or the water including the adjusted pH (such as the pH buffer solution) with a weight ratio of the mushroom waste substrate in 1 to 100% w/v; agitating the water including the mushroom waste substrate dispersed therein immediately or for approximately two (2) hours; and collecting a supernatant liquor. Herein, the mushroom waste substrate can be simply dispersed in the water without comminution thereof. The supernatant liquor can be collected at a room temperature or low temperature. The mushroom waste substrate can be comminuted by a commitution device such as the vibrating ball mill, the rotating ball mill, the planetary ball mill, the roll mill, the disk mill, the bead mill, the vane-type high speed rotating mixer, or the homo mixer. A size of the mushroom waste substrate to be comminuted can be any size as long as the cellulase group in the mushroom waste substrate is extracted.

The saccharification step 50 allows an enzyme group extract solution obtained by the immersion agitation step 40 to be provided into the mixed solution formed of mixture of the lignocellulose resource and the solution by the mixing step 30 to purify the saccharified solution by the enzymatic saccharification reaction. Herein the enzyme group extract solution represents an extraction solution of the enzyme group derived from the mushroom waste substrate. The enzyme group is provided into the mixed solution, so that the cellulose or the xylan in the mixed solution is hydrolyzed, and cello-oligosaccharide, cellobiose, glucose, chitobiose, chito-oligosaccharide, and xylose are generated. The saccharification step 50 can be performed in a batch-wise manner or a continuous manner using a bioreactor including an immobilized enzyme.

In a case where the cellulose or the xylan is hydrolyzed using the enzyme derived from the mushroom waste substrate, the hydrolyzation can be performed under conditions which are usually used for a degradation method of the cellulose or the xylan into the glucose or the xylose. Although the cellulase group has a characteristic that varies depending on the mushroom waste substrate to be used, an optimum pH range thereof is between 4.0 and 7.5, and an optimum temperature range thereof is between 20.0 and 40.0 degrees Celsius. Accordingly, the mixed solution of the mixing step 30 is adjusted in the saccharification step 50 in such a manner that the pH thereof is ranged between 4.0 and 7.0. Moreover, the pH and the temperature in the reaction system are adjusted in the saccharification step 50 in such a manner as to be within the optimum pH range and the optimum temperature range of the enzyme so that the enzyme saccharification reaction is smoothly performed.

The fermentation step 60 allows the glucose or the xylose in the saccharified solution to be fermented by providing the yeast or bacterium into the saccharified solution generated in the saccharification step 50, thereby generating the ethanol. The fermentation is performed using the yeast or the bacterium. Herein, any yeast or any bacterium can be used for the fermentation as long the ethanol is generated from the glucose or the xylose in the saccharified solution. For example, bakery yeast can be used. Moreover, one type of the yeast or the bacterium can be used alone, or a combination of different types of the yeasts or the bacteria can be used. A temperature for the fermentation can be changed as necessary according to the yeast or yeasts or the bacterium or bacteria to be used.

The distillation step 70 allows a fermentation solution obtained by the fermentation step 60 to be distilled, thereby purifying the ethanol.

According the method for producing the ethanol of the present invention, the lignocellulose resource serving as a raw material is distilled with the steam (steam distillation step 10), and the effluent component in the lignocellulose resource is flowed out. Subsequently, the lignocellulose resource is comminuted (comminution step 20).

The comminuted lignocellulose resource is mixed with the solution or the liquid medium such as water without any washing treatment and the like (mixing step 30), and the pH of the mixed solution is adjusted in such a manner as to be within the optimum pH range of the enzyme. According to the present invention, the impurities adhered to the lignocellulose resource is removed by the steam distillation, so that the washing treatment is not necessarily performed for the impurity removal before the lignocellulose resource and the solution are mixed. Therefore, the saccharified solution is easily generated.

The extraction solution obtained in the course of extracting the enzyme group from the mushroom waste substrate (immersion agitation step 40) is provided into the mixed solution of the lignocellulose resource and the solution as described above, so that the pH of the mixed solution is controlled in such a manner as to remain in the optimum temperature range and the optimum pH range of the enzyme, and the cellulose or the xylan is hydrolyzed, thereby generating the saccharified solution (saccharification step 50). Herein, the cellulase group serving as the enzyme can be once purified from the extraction solution obtained in the course of extracting the enzyme from the mushroom waste substrate, and the purified cellulase group can be provided into the mixed solution of the lignocellulose resource and the solution.

Subsequently, the yeast or the bacterium is provided into the saccharified solution purified by the enzyme derived from the mushroom waste substrate to perform the fermentation (fermentation step 60). Accordingly, the glucose or the xylose in the saccharified solution is converted into the ethanol, and an ethanol-containing substance including the ethanol is obtained. The ethanol-containing substance, for example, undergoes the distillation to separate the ethanol therefrom (distillation step 70), and the ethanol of high density is obtained.

What is claimed is:

1. A method for producing ethanol, comprising:
   a step of deriving an enzyme group from a mushroom waste substrate;
   a saccharification step allowing a saccharified solution to be generated from a lignocellulose resource by an enzymatic saccharification reaction using the enzyme group derived from a mushroom waste substrate; and
   a fermentation step allowing an ethanol to be generated by fermentation of the saccharified solution generated by the saccharification step.

2. The method for producing ethanol according to claim 1, wherein the enzyme group includes a cellulase group.

3. The method for producing ethanol according to claim 1, wherein the enzyme group includes a xylanase group.

4. The method for producing ethanol according to claim 1, wherein the lignocellulose resource to be used for the saccharification step is comminuted after steam distillation and an effluent component resulting from the steam distillation is removed.

5. The method for producing ethanol according to claim 4, wherein the steam distillation of the lignocellulose resource and the comminution of the lignocellulose resource are alternately performed for plural times.

6. The method for producing ethanol according to claim 1, the saccharification step allows an extraction solution obtained in the course of extracting the enzyme group from the mushroom waste substrate to be provided into a mixed solution of the lignocellulose resource and a liquid medium, and allow the saccharified solution to be generated by the enzymatic saccharification reaction.

7. A method for producing ethanol, comprising the steps of:
   (a) heating a lignocellulose resource;
   (b) removing an effluent component resulting from step (a);

(c) deriving at least one enzyme from a mushroom waste substrate that was previously used for growing mushrooms;
(d) producing a mixture that includes a liquid, the at least one enzyme, and the lignocellulose resource after the removal of the effluent component;
(e) permitting the mixture to saccharify;
(f) fermenting the saccharified mixture to produce a fermented mixture; and
(g) distilling the fermented mixture.

8. The method of claim 7, further comprising the step of pulverizing the lignocellulose resource before step (b) is conducted.

9. The method of claim 7, wherein the at least one enzyme includes cellulase.

10. The method of claim 7, wherein the at least one enzyme includes xylanase.

11. The method of claim 7, wherein the at least one enzyme includes cellulase and xylanase.

12. the method of claim 7, wherein step (a) is conducted using steam.

* * * * *